(12) United States Patent
Meade et al.

(10) Patent No.: US 10,098,630 B2
(45) Date of Patent: Oct. 16, 2018

(54) APPARATUS AND METHOD FOR MINIMALLY INVASIVE SUTURING

(71) Applicant: ENDOEVOLUTION, LLC, Raynham, MA (US)

(72) Inventors: John C. Meade, Mendon, MA (US); Gerald I. Brecher, N. Andover, MA (US)

(73) Assignee: EndoEvolution, LLC, Raynham, MA (US)

( * ) Notice: Subject to any disclaimer, the term of this patent is extended or adjusted under 35 U.S.C. 154(b) by 0 days.

(21) Appl. No.: 15/828,431

(22) Filed: Nov. 30, 2017

(65) Prior Publication Data

US 2018/0103946 A1    Apr. 19, 2018

Related U.S. Application Data

(63) Continuation-in-part of application No. 15/480,945, filed on Apr. 6, 2017, now Pat. No. 9,936,944, which
(Continued)

(51) Int. Cl.
*A61B 17/04* (2006.01)
*A61B 17/34* (2006.01)
(Continued)

(52) U.S. Cl.
CPC ...... *A61B 17/0469* (2013.01); *A61B 17/0482* (2013.01); *A61B 17/0491* (2013.01);
(Continued)

(58) Field of Classification Search
CPC ............ A61B 17/0469; A61B 17/0491; A61B 17/06066; A61B 17/0625;
(Continued)

(56) References Cited

U.S. PATENT DOCUMENTS

| 1,327,577 A | 1/1920 | Turner |
| 1,822,330 A | 9/1931 | Ainslie |

(Continued)

FOREIGN PATENT DOCUMENTS

| CN | 2169381 | 6/1994 |
| CN | 201082170 | 7/2008 |

(Continued)

OTHER PUBLICATIONS

International Preliminary Report on Patentability dated Jan. 13, 2008 and Written Opinion dated Jun. 13, 2008 for PCT/US05/33507.

(Continued)

*Primary Examiner* — Gregory Anderson
(74) *Attorney, Agent, or Firm* — Crawford Maunu PLLC

(57) ABSTRACT

The invention includes a needle loader that may be used with a suturing device. The needle loader includes a generally planar needle supporting surface, a hub configured and adapted for receiving a generally toroidally shaped suturing needle around the hub, and means for retaining a suturing needle in a fixed toroidal rotational position with respect to the hub about a center axis of needle rotation. Generally, a needle mounted around the hub is selectively disposable on and removable from the hub. In accordance with a further aspect, the loader may further include an opening for retaining suture material attached to a suturing needle. The opening may include a groove defined through the needle supporting surface. The needle loader may further include a guard for preventing access to the point of a suturing needle to protect the needle and/or to prevent accidental needle sticks.

20 Claims, 4 Drawing Sheets

Related U.S. Application Data is a continuation of application No. 15/480,561, filed on Apr. 6, 2017, now Pat. No. 9,795,376, which is a continuation of application No. 15/357,375, filed on Nov. 21, 2016, now Pat. No. 9,700,301, which is a continuation of application No. 15/265,650, filed on Sep. 14, 2016, now Pat. No. 9,597,071, which is a continuation of application No. 14/796,642, filed on Jul. 10, 2015, now Pat. No. 9,474,523, which is a continuation of application No. 14/472,090, filed on Aug. 28, 2014, now Pat. No. 9,451,948, which is a continuation of application No. 13/361,444, filed on Jan. 30, 2012, now Pat. No. 8,821,519, which is a continuation of application No. 12/592,174, filed on Nov. 20, 2009, now Pat. No. 8,123,764, which is a continuation-in-part of application No. 12/175,442, filed on Jul. 17, 2008, now Pat. No. 7,976,555.

(51) Int. Cl.
*A61B 34/00* (2016.01)
*A61B 17/29* (2006.01)
*A61B 17/062* (2006.01)
*A61B 17/06* (2006.01)
*A61B 17/00* (2006.01)

(52) U.S. Cl.
CPC .... *A61B 17/0625* (2013.01); *A61B 17/06066* (2013.01); *A61B 17/29* (2013.01); *A61B 17/34* (2013.01); *A61B 34/71* (2016.02); *A61B 2017/0023* (2013.01); *A61B 2017/00398* (2013.01); *A61B 2017/00407* (2013.01); *A61B 2017/00473* (2013.01); *A61B 2017/047* (2013.01); *A61B 2017/0474* (2013.01); *A61B 2017/0608* (2013.01); *A61B 2017/06028* (2013.01); *A61B 2017/06085* (2013.01); *A61B 2017/2923* (2013.01); *A61B 2017/2927* (2013.01); *A61B 2017/2943* (2013.01); *A61B 2217/007* (2013.01)

(58) Field of Classification Search
CPC .. A61B 2017/0023; A61B 2017/00407; A61B 2017/00473; A61B 2017/06028
See application file for complete search history.

(56) References Cited

U.S. PATENT DOCUMENTS

| | | | |
|---|---|---|---|
| 2,327,353 A | 8/1943 | Karle | |
| 2,601,564 A | 6/1952 | Smith | |
| 3,197,997 A | 8/1965 | Kurtz | |
| 3,311,110 A | 3/1967 | Singerman et al. | |
| 3,344,790 A | 10/1967 | Darner | |
| 3,762,418 A | 10/1973 | Wasson | |
| 3,834,599 A | 9/1974 | Herr | |
| 3,835,912 A | 9/1974 | Kristensen et al. | |
| 3,910,282 A | 10/1975 | Messer et al. | |
| 3,951,261 A | 4/1976 | Mandel et al. | |
| 3,972,418 A | 8/1976 | Schuler et al. | |
| 4,027,608 A | 6/1977 | Arbuckle | |
| 4,074,732 A | 2/1978 | Wilkens | |
| 4,235,177 A | 11/1980 | Arbuckle | |
| 4,327,655 A | 5/1982 | Addy et al. | |
| 4,331,277 A | 5/1982 | Green | |
| 4,437,465 A | 3/1984 | Nomoto et al. | |
| 4,509,945 A | 4/1985 | Kramann et al. | |
| 4,527,564 A | 7/1985 | Eguchi et al. | |
| 4,557,265 A | 12/1985 | Andersson | |
| 4,621,640 A | 11/1986 | Mulhollan et al. | |
| 4,841,888 A | 6/1989 | Mills et al. | |
| 4,899,746 A | 2/1990 | Brunk | |
| 4,957,502 A | 9/1990 | Takase | |
| 5,080,663 A | 1/1992 | Mills et al. | |
| 5,089,012 A | 2/1992 | Prou | |
| 5,174,300 A | 12/1992 | Bales | |
| 5,201,760 A | 4/1993 | West | |
| 5,210,376 A | 5/1993 | Caviar | |
| 5,269,806 A | 12/1993 | Sardelis et al. | |
| 5,305,281 A | 4/1994 | Lubeck | |
| 5,306,281 A | 4/1994 | Beurrier | |
| 5,308,353 A | 5/1994 | Beurrier | |
| 5,318,566 A | 6/1994 | Miller | |
| 5,318,578 A | 6/1994 | Hasson | |
| 5,330,502 A | 7/1994 | Hassler | |
| 5,344,061 A | 9/1994 | Crainich | |
| 5,358,498 A | 10/1994 | Shave | |
| 5,364,408 A | 11/1994 | Gordon | |
| 5,373,101 A | 12/1994 | Barabolak | |
| 5,376,101 A | 12/1994 | Green et al. | |
| 5,387,221 A | 2/1995 | Bisgaard | |
| 5,403,344 A | 4/1995 | Allen | |
| 5,437,681 A | 8/1995 | Meade et al. | |
| 5,454,819 A | 10/1995 | Knoepfler | |
| 5,462,558 A | 10/1995 | Kolesa et al. | |
| 5,472,081 A | 12/1995 | Kilgrow et al. | |
| 5,474,568 A | 12/1995 | Scott | |
| 5,478,344 A | 12/1995 | Stone et al. | |
| 5,478,345 A | 12/1995 | Stone et al. | |
| 5,480,409 A | 1/1996 | Riza | |
| 5,503,266 A | 4/1996 | Kalbfeld et al. | |
| 5,514,159 A | 5/1996 | Matula et al. | |
| 5,540,705 A | 7/1996 | Meade et al. | |
| 5,571,119 A | 11/1996 | Atala | |
| 5,575,800 A | 11/1996 | Gordon | |
| 5,578,044 A | 11/1996 | Gordon et al. | |
| 5,643,295 A | 7/1997 | Yoon | |
| 5,645,552 A | 7/1997 | Sherts | |
| 5,665,096 A | 9/1997 | Yoon | |
| 5,665,109 A | 9/1997 | Yoon | |
| 5,669,490 A | 9/1997 | Colligan et al. | |
| 5,675,961 A | 10/1997 | Cerwin et al. | |
| 5,709,693 A | 1/1998 | Taylor | |
| 5,713,910 A | 2/1998 | Gordon et al. | |
| 5,715,942 A | 2/1998 | Li et al. | |
| 5,741,277 A | 4/1998 | Gordon et al. | |
| 5,755,729 A | 5/1998 | de la Torre et al. | |
| 5,759,188 A | 6/1998 | Yoon | |
| 5,766,186 A | 6/1998 | Faraz et al. | |
| 5,814,069 A | 9/1998 | Schulze et al. | |
| 5,814,071 A | 9/1998 | McDevitt et al. | |
| 5,830,234 A | 11/1998 | Wojciechowicz et al. | |
| 5,833,695 A | 11/1998 | Yoon | |
| 5,860,992 A | 1/1999 | Daniel et al. | |
| 5,891,160 A | 4/1999 | Williamson, IV et al. | |
| 5,906,273 A | 5/1999 | Pohle et al. | |
| 5,908,426 A | 6/1999 | Pierce | |
| 5,908,428 A | 6/1999 | Scirica et al. | |
| 5,911,727 A | 6/1999 | Taylor | |
| 5,954,733 A | 9/1999 | Yoon | |
| 5,968,077 A | 10/1999 | Wojciechowicz et al. | |
| 5,993,466 A | 11/1999 | Yoon | |
| 6,016,905 A | 1/2000 | Gemma et al. | |
| 6,036,694 A | 3/2000 | Goble et al. | |
| 6,048,351 A | 4/2000 | Gordon et al. | |
| 6,053,908 A | 4/2000 | Crainich et al. | |
| 6,056,771 A | 5/2000 | Proto | |
| 6,071,289 A | 6/2000 | Stefanchik et al. | |
| 6,096,051 A | 8/2000 | Kortenbach et al. | |
| 6,126,666 A | 10/2000 | Trapp et al. | |
| 6,135,385 A | 10/2000 | Martinez de Lahidalga | |
| 6,136,010 A | 10/2000 | Modesitt et al. | |
| 6,159,224 A | 12/2000 | Yoon | |
| 6,261,307 B1 | 7/2001 | Yoon et al. | |
| 6,270,508 B1 | 8/2001 | Klieman et al. | |
| 6,322,581 B1 | 11/2001 | Fukuda et al. | |
| 6,332,888 B1 | 12/2001 | Levy et al. | |
| 6,346,111 B1 | 2/2002 | Gordon et al. | |
| 6,443,962 B1 | 9/2002 | Gaber | |
| 6,454,777 B1 | 9/2002 | Green | |
| 6,454,778 B2 | 9/2002 | Kortenbach | |

(56) References Cited

U.S. PATENT DOCUMENTS

| | | |
|---|---|---|
| 6,494,888 B1 | 12/2002 | Laufer et al. |
| 6,506,196 B1 | 1/2003 | Laufer |
| 6,558,400 B2 | 5/2003 | Deem et al. |
| 6,656,194 B1 | 12/2003 | Gannoe et al. |
| 6,663,639 B1 | 12/2003 | Laufer et al. |
| 6,719,763 B2 | 4/2004 | Chung et al. |
| 6,719,764 B1 | 4/2004 | Gellman et al. |
| 6,746,460 B2 | 6/2004 | Gannoe et al. |
| 6,755,843 B2 | 6/2004 | Chung et al. |
| 6,835,200 B2 | 12/2004 | Laufer et al. |
| 6,877,352 B1 | 4/2005 | Schlereth |
| 6,908,427 B2 | 6/2005 | Fleener et al. |
| 6,923,819 B2 | 8/2005 | Meade et al. |
| 6,955,643 B2 | 10/2005 | Gellman et al. |
| 7,004,951 B2 | 2/2006 | Gibbens, III |
| 7,033,370 B2 | 4/2006 | Gordon et al. |
| 7,041,111 B2 | 5/2006 | Chu |
| 7,144,401 B2 | 12/2006 | Yamamoto et al. |
| 7,166,116 B2 | 1/2007 | Lizardi et al. |
| 7,338,504 B2 | 3/2008 | Gibbens et al. |
| 7,615,060 B2 | 11/2009 | Stokes et al. |
| 7,628,796 B2 | 12/2009 | Shelton, IV et al. |
| 7,637,909 B2 | 12/2009 | Lechot et al. |
| 7,766,925 B2 | 8/2010 | Stokes et al. |
| 7,828,812 B2 | 11/2010 | Stokes et al. |
| 7,833,236 B2 | 11/2010 | Stokes et al. |
| 7,846,169 B2 | 12/2010 | Shelton, IV et al. |
| 7,862,572 B2 | 1/2011 | Meade et al. |
| 7,887,554 B2 | 2/2011 | Stokes et al. |
| 7,976,533 B2 | 7/2011 | Larsson |
| 7,976,555 B2 | 7/2011 | Meade et al. |
| 7,993,354 B1 | 8/2011 | Brecher et al. |
| 8,066,737 B2 | 11/2011 | Meade et al. |
| 8,123,764 B2 | 2/2012 | Meade et al. |
| 8,469,973 B2 | 6/2013 | Meade et al. |
| 8,500,756 B2 | 8/2013 | Papa et al. |
| 8,623,048 B2 | 1/2014 | Brecher et al. |
| 8,641,728 B2 | 2/2014 | Stokes et al. |
| 8,702,732 B2 | 4/2014 | Woodard, Jr. et al. |
| 8,906,043 B2 | 12/2014 | Woodard, Jr. et al. |
| 9,125,645 B1 | 9/2015 | Martin et al. |
| 9,173,655 B2 | 11/2015 | Martin |
| 9,220,496 B2 | 12/2015 | Martin et al. |
| 9,357,998 B2 | 6/2016 | Martin et al. |
| 9,370,354 B1 | 6/2016 | Martin et al. |
| 9,375,212 B2 | 6/2016 | Martin et al. |
| 9,398,905 B2 | 7/2016 | Martin |
| 9,427,226 B2 | 8/2016 | Martin et al. |
| 9,427,227 B2 | 8/2016 | Martin et al. |
| 9,445,807 B2 | 9/2016 | Brecher et al. |
| 9,451,948 B2 | 9/2016 | Meade et al. |
| 9,474,522 B2 | 10/2016 | Deck et al. |
| 9,474,523 B2 | 10/2016 | Meade et al. |
| 9,486,209 B2 | 11/2016 | Martin et al. |
| 9,498,207 B2 | 11/2016 | Martin et al. |
| 9,526,495 B2 | 12/2016 | Martin et al. |
| 2002/0107530 A1 | 8/2002 | Sauer et al. |
| 2002/0116011 A1 | 8/2002 | Chung et al. |
| 2002/0173800 A1 | 11/2002 | Dreyfuss et al. |
| 2002/0193809 A1 | 12/2002 | Meade et al. |
| 2002/0198542 A1 | 12/2002 | Yamamoto et al. |
| 2003/0083674 A1 | 5/2003 | Gibbens |
| 2003/0105475 A1 | 6/2003 | Sancoff et al. |
| 2003/0171760 A1 | 9/2003 | Gambale |
| 2003/0181924 A1 | 9/2003 | Yamamoto et al. |
| 2003/0233104 A1 | 12/2003 | Gellman et al. |
| 2003/0233108 A1 | 12/2003 | Gellman et al. |
| 2004/0034369 A1 | 2/2004 | Sauer et al. |
| 2004/0034372 A1 | 2/2004 | Chu |
| 2004/0044354 A1 | 3/2004 | Gannoe et al. |
| 2004/0059350 A1 | 3/2004 | Gordon et al. |
| 2004/0082963 A1 | 4/2004 | Gannoe et al. |
| 2004/0088008 A1 | 5/2004 | Gannoe et al. |
| 2004/0122473 A1 | 6/2004 | Ewers et al. |
| 2004/0138682 A1 | 7/2004 | Onuki et al. |
| 2004/0147941 A1 | 7/2004 | Takemoto et al. |
| 2004/0147958 A1 | 7/2004 | Lam et al. |
| 2004/0162568 A1 | 8/2004 | Saadat et al. |
| 2004/0181243 A1 | 9/2004 | Chu et al. |
| 2004/0194790 A1 | 10/2004 | Laufer et al. |
| 2004/0210243 A1 | 10/2004 | Gannoe et al. |
| 2004/0260344 A1 | 12/2004 | Lyons et al. |
| 2005/0015101 A1 | 1/2005 | Gibbens et al. |
| 2005/0035007 A1 | 2/2005 | Kennedy et al. |
| 2005/0055038 A1 | 3/2005 | Kelleher et al. |
| 2005/0070931 A1 | 3/2005 | Li et al. |
| 2005/0075653 A1 | 4/2005 | Saadat et al. |
| 2005/0262984 A1 | 12/2005 | Hetcher et al. |
| 2006/0069396 A1 | 3/2006 | Meade et al. |
| 2006/0111732 A1 | 5/2006 | Gibbens et al. |
| 2006/0224184 A1 | 10/2006 | Stefanchik et al. |
| 2006/0282089 A1 | 12/2006 | Stokes et al. |
| 2006/0282090 A1 | 12/2006 | Stokes et al. |
| 2006/0282091 A1 | 12/2006 | Shelton et al. |
| 2006/0282092 A1 | 12/2006 | Stokes et al. |
| 2006/0282093 A1 | 12/2006 | Shelton et al. |
| 2006/0282094 A1 | 12/2006 | Stokes et al. |
| 2006/0282095 A1 | 12/2006 | Stokes et al. |
| 2006/0282096 A1 | 12/2006 | Papa et al. |
| 2006/0282097 A1 | 12/2006 | Ortiz et al. |
| 2006/0282098 A1* | 12/2006 | Shelton, IV ........ A61B 1/00087 606/144 |
| 2006/0282099 A1 | 12/2006 | Stokes et al. |
| 2007/0135838 A1 | 6/2007 | Meyer |
| 2008/0132919 A1 | 6/2008 | Chui et al. |
| 2008/0140091 A1 | 6/2008 | Dedeyne et al. |
| 2009/0024145 A1 | 1/2009 | Meade et al. |
| 2010/0036415 A1 | 2/2010 | Cabezas |
| 2010/0049219 A1 | 2/2010 | Cronin et al. |
| 2010/0130990 A1 | 5/2010 | Saliman |
| 2010/0152751 A1 | 6/2010 | Meade et al. |
| 2014/0171977 A1 | 6/2014 | Martin et al. |
| 2014/0171979 A1 | 6/2014 | Martin et al. |
| 2014/0172015 A1 | 6/2014 | Martin et al. |
| 2015/0133967 A1 | 5/2015 | Martin |
| 2015/0351745 A1 | 12/2015 | Mumaw et al. |
| 2015/0351746 A1 | 12/2015 | Martin et al. |
| 2015/0351749 A1 | 12/2015 | Martin et al. |
| 2015/0351756 A1 | 12/2015 | Martin et al. |
| 2016/0317148 A1 | 11/2016 | Martinez |
| 2016/0331374 A1 | 11/2016 | Martin et al. |
| 2016/0345958 A1 | 12/2016 | Martin et al. |
| 2016/0346827 A1 | 12/2016 | Martin et al. |
| 2016/0361055 A1 | 12/2016 | Martin et al. |
| 2016/0367238 A1 | 12/2016 | Deck et al. |
| 2016/0367239 A1 | 12/2016 | Mumaw et al. |
| 2016/0367240 A1 | 12/2016 | Shelton, IV et al. |
| 2016/0367243 A1 | 12/2016 | Martin et al. |

FOREIGN PATENT DOCUMENTS

| | | |
|---|---|---|
| DE | 4310315 | 10/1993 |
| EP | 0648474 | 4/1995 |
| EP | 1733685 A1 | 12/2006 |
| EP | 1839591 A1 | 10/2007 |
| EP | 2103262 | 9/2009 |
| EP | 05797831 | 2/2011 |
| EP | 10009832 | 2/2011 |
| EP | 2292157 | 3/2011 |
| EP | 2308391 | 4/2011 |
| EP | 2370002 | 10/2011 |
| EP | 1791476 | 12/2015 |
| FR | 2540377 | 8/1984 |
| GB | 18602 | 9/1908 |
| JP | 556270 | 1/1980 |
| JP | 55151956 | 11/1980 |
| JP | 07178100 | 7/1995 |
| JP | 07328021 | 12/1995 |
| JP | H11276492 | 10/1999 |
| JP | 2000139931 | 5/2000 |
| JP | 2005080761 | 3/2005 |
| JP | 2005253987 | 9/2005 |
| WO | WO9609796 | 4/1996 |
| WO | WO9609796 A2 | 4/1996 |

(56) References Cited

FOREIGN PATENT DOCUMENTS

| | | |
|---|---|---|
| WO | WO9729694 | 8/1997 |
| WO | WO9912482 | 3/1999 |
| WO | WO9940850 | 8/1999 |
| WO | WO9947050 | 9/1999 |
| WO | WO0112084 | 2/2001 |
| WO | WO02102226 | 12/2002 |
| WO | WO2003028541 | 10/2003 |
| WO | WO2004012606 | 2/2004 |
| WO | WO2004021894 | 3/2004 |
| WO | WO2004028402 | 4/2004 |
| WO | WO2004086986 | 10/2004 |
| WO | WO2006034209 | 3/2006 |
| WO | WO2007089603 | 8/2007 |
| WO | WO2008147555 | 12/2008 |
| WO | WO2010062380 | 6/2010 |

OTHER PUBLICATIONS

International Preliminary Report on Patentability dated Jan. 27, 2006 and Written Opinion dated Nov. 1, 2007 for PCT/US07/02204.
International Search Report and Written Opinion dated Mar. 3, 2003 for PCT/US02/12560.
International Preliminary Examination Report dated Mar. 12, 2004 for PCT/US02/12560.
International Search Report and Written Opinion dated Jul. 5, 2010 for PCT/US09/06212.
Supplemental European Search Report dated Mar. 15, 2007 for EP140654.5.
European Search Report dated Feb. 8, 2011 for EP10009831.8.
European Search Report dated Feb. 9, 2011 for EP10009832.6.
Office Action dated Jul. 1, 2014 from Corresponding Japanese Application No. 2013-138559.
European Search Report dated Jun. 5, 2015 from corresponding European Application No. 12822057.1.
European Search Report dated Aug. 14, 2015 from corresponding European Application No. 11830008.
International Search Report issued in related PCT application No. PCT/US07/002204 dated Nov. 1, 2007.
Written Opinion issued in related PCT application No. PCT/US07/002204 dated Nov. 1, 2007.
Search Report dated May 20, 2010 from SG Application No. 200805426-4.
Extended Search Report dated Feb. 17, 2011 from corresponding European Application No. 05797831.4.
Extended Search Report dated Feb. 21, 2011 from corresponding European Application No. 10009831.8.
Extended Search Report dated Feb. 21, 2011 from corresponding European Application No. 10009832.6.
European Search Report dated Mar. 11, 2011 from corresponding European Application No. 07762862.6.
Japanese Office Action dated Oct. 18, 2011 from Corresponding Japanese Application No. 2008-552444.
International Preliminary Report on Patentability dated Feb. 11, 2014 from Corresponding Application No. PCT PCT/US12/049979.
International Search Report and Written Opinion of the International Searching Authority (ISA) dated Apr. 24, 2012 relating to PCT/US11/054334.
Examination Report issued by Hungarian IP Office on behalf of Singapore IP Office dated Feb. 8, 2012 in connection with Singapore Application No. 200907505-2.
Supplementary European Search Report dated Mar. 23, 2007 in connection with EP Application No. 02725747.6.
Supplementary European Search Report dated Oct. 6, 2009 in connection with EP Application No. 02725747.6.
Office Action with English translation in connection with Japanese Patent Application No. JP2007-532595 dated Jan. 1, 2011.
Extended Search Report in connection with EP05797831.4 dated Feb. 25, 2011.
Written Opinion dated Jan. 11, 2011 in connection with Singapore Patent Application No. 200907505-2.
International Search Report and Written Opinion dated Jan. 5, 2009 in connection with PCT/US08/006674.
International Preliminary Report on Patentability dated Nov. 24, 2009 in connection with PCT/US08/006674.
International Search Report issued in related PCT application No. PCT/US09/006212 dated Jul. 5, 2010.
International Search Report issued in related PCT application No. PCT/US05/33507 dated Jun. 13, 2008.
Extended Search Report dated Nov. 29, 2012 from corresponding European Application No. 09829467.1.
Ethicon Exhibit 1001 in IPR Case No. 2016-00071; U.S. Pat. No. 6,923,819, issued Aug. 2, 2005, 32 pages.
Ethicon Exhibit 1002 in IPR Case No. 2016-00071; Prosecution History of U.S. Appl. No. 10/127,254, filed Apr. 22, 2002, 359 pages.
Ethicon Exhibit 1003 in IPR Case No. 2016-00071; Expert Declaration of Kevin L. Houser, M.S., dated Oct. 22, 2015, 105 pages.
Ethicon Exhibit 1004 in IPR Case No. 2016-00071; U.S. Pat. No. 5,437,681, issued Aug. 1,1995, 15 pages.
Ethicon Exhibit 1005 in IPR Case No. 2016-00071; U.S. Pat. No. 5,306,281, dated Apr. 26, 1994, 12 pages.
Ethicon Exhibit 1006 in IPR Case No. 2016-00071; U.S. Pat. No. 4,557,265, issued Dec. 10, 1985, 4 pages.
Ethicon Exhibit 1007 in IPR Case No. 2016-00071; U.S. Pat. No. 6,053,908, issued Apr. 25, 2000, 9 pages.
Ethicon Exhibit 1008 in IPR Case No. 2016-00071; U.S. Pat. No. 5,911,727, issued Jun. 15, 1999, 12 pages.
Ethicon Exhibit 1009 in IPR Case No. 2016-00071; N. Chironis, Mechanisms, Linkages, and Mechanical Control, 5th ed. 1965, 8 pages.
Ethicon Exhibit 1010 in IPR Case No. 2016-00071; "Webster's New Universal Unabridged Dictionary," 2nd Edition 1983, 4 pages.
Exhibit 2001 in IPR Case No. 2016-00071; U.S. Pat. No. 5,709,693, issued Jan. 20, 1998, 7 pages.
Petition for Inter Partes Review of U.S. Pat. No. 6,923,819, dated Oct. 22, 2015, 64 pages.
Patent Owner's Preliminary Response in IPR Case No. 2016-00071, dated Jan. 29, 2016, 49 pages.
Decision on Petition For Inter Partes Review of U.S. Pat. No. 6,923,819 in IPR Case No. 2016-00071, dated Apr. 28, 2016, 17 pages.
Non-Final Office Action in U.S. Appl. No. 15/260,094, dated Jan. 17, 2017, 14 pages.
Preliminary Amendment filed in U.S. Appl. No. 15/260,094, dated Nov. 18, 2016, 7 pages.
Decision of Refusal issued in JP Application No. 2015-112857, dated Dec. 8, 2016, 3 pages.
Japanese Office Action dated Oct. 18, 2017, from Japanese patent application No. 2016-187970.

* cited by examiner

APPARATUS AND METHOD FOR MINIMALLY INVASIVE SUTURING

CROSS-REFERENCE TO RELATED APPLICATIONS

This Application is a continuation-in-part of and claims the benefit of priority to Ser. No. 15/480,945, filed Apr. 6, 2017, now U.S. Pat. No. 9,936,944, which in turn is a continuation of and claims the benefit of priority to U.S. patent application Ser. No. 15/480,561, filed Apr. 6, 2017, now U.S. Pat. No. 9,795,376, which in turn is a continuation of and claims the benefit of priority to U.S. patent application Ser. No. 15/357,375, filed Nov. 21, 2016, now U.S. Pat. No. 9,700,301, which in turn is a continuation of and claims the benefit of priority to U.S. patent application Ser. No. 15/265,650, now U.S. Pat. No. 9,597,071, filed Sep. 14, 2016, which is a continuation of and claims the benefit of priority to U.S. patent application Ser. No. 14/796,642, filed Jul. 10, 2015, now U.S. Pat. No. 9,474,523, which is a continuation of and claims the benefit of priority to U.S. patent application Ser. No. 14/472,090, filed Aug. 28, 2014, now U.S. Pat. No. 9,451,948, which is a continuation of and claims the benefit of priority to U.S. patent application Ser. No. 13/361,444 filed Jan. 30, 2012, now U.S. Pat. No. 8,821,519, which is a continuation of and claims the benefit of priority to U.S. patent application Ser. No. 12/592,174, filed on Nov. 20, 2009, now U.S. Pat. No. 8,123,764, which is a continuation-in-part of and claims the benefit of priority to U.S. patent application Ser. No. 12/175,442, filed Jul. 17, 2008.

This application is related to U.S. patent application Ser. No. 11/231,135, filed Sep. 20, 2005, which claims the benefit of priority to U.S. Provisional Application Ser. No. 60/611,362, filed Sep. 20, 2004. This application is also related to U.S. Provisional Application Ser. No. 60/939,887, filed May 24, 2007. Each of the aforementioned patent applications is incorporated by reference herein in its entirety for any purpose whatsoever.

BACKGROUND OF THE INVENTION

Minimally invasive surgery (MIS) has allowed physicians to carry out many surgical procedures with less pain and disability than conventional, open surgery. Unlike conventional open surgery, where the surgical site is readily accessible through a large incision, enabling the surgeon to easily visualize and manipulate both tissue and instruments, MIS requires the surgeon to operate remotely by inserting and manipulating instruments through small punctures ("keyhole surgery") or through natural orifices, including the vagina, the esophagus, or the anus.

In MIS, a small puncture is typically made in the body. Medical instruments are then inserted through a cannula. A cannula has a small inside diameter, typically 5-10 millimeters (mm), and sometimes up to 20 millimeters (mm) or more. A number of such cannulas are inserted into the body for any given operation. Minimally invasive surgical instruments are necessarily smaller, and are also generally longer and therefore are more difficult to manipulate with precision.

Perhaps the most problematic surgical task in MIS is suturing. Suturing requires coordinated manipulation with both hands of small needles and sutures that are difficult to visualize (particularly when only indirect, two-dimensional video imaging is available) as well as the several instruments (including needle-drivers and pick-up forceps) ordinarily used to suture by hand. In an environment characterized by limited space, limited visualization, and limited mobility, many surgeons find minimally invasive suturing by hand an extremely difficult, often virtually impossible, surgical task.

In the preferred method of suturing by hand, a grasping forceps ("needle driver") is held by the surgeon and is used to grip a curved needle near the needle's tail. Pronation of the surgeon's wrist drives the needle into the tissue. When the point of the curved needle emerges from the tissue, the surgeon releases the needle from the grip of the needle driver and grasps the point with another forceps ("pick-ups"). The surgeon then pulls the curved needle by the needle point, preferably in a circular path following the arc of the needle's curvature to follow the most atraumatic path through the tissue, until the entire length of the needle has exited the tissue. Each time a stitch is placed, the curved needle is thus driven around in a complete circular arc. Individual (interrupted) stitches are placed by tying off the suture following the placement of each stitch. Running (continuous) stitches are placed by repeatedly driving the curved needle in a complete circular arc repeatedly until the desired length of suture and number of stitches has been placed. In order to place additional interrupted or continuous stitches, the surgeon must let go of the point of the needle and re-grasp the needle near the needle's tail.

In the manual suturing technique described above, the direct handling of the needle can result in accidental needle pricks through a surgeon or nurse's gloves, posing a potential risk of infection for the surgeon, nurse, staff, and patient, or cause the needle to become contaminated with pathogenic bacteria that can cause onset of infection at the site of the sutures. There is also a risk of the needle penetrating internal organs or vessels and causing a serious, and often fatal infection.

Various devices for suturing for MIS are described in U.S. Pat. No. 5,643,295 entitled "Methods and Apparatus for Suturing Tissue"; U.S. Pat. No. 5,665,096 entitled "Needle Driving Apparatus and Methods of Suturing Tissue"; U.S. Pat. No. 5,665,109 entitled "Methods and Apparatus for Suturing Tissue"; U.S. Pat. No. 5,759,188 entitled "Suturing Instrument with Rotatably Mounted Needle Driver and Catcher"; U.S. Pat. No. 5,860,992 entitled "Endoscopic Suturing Devices and Methods"; U.S. Pat. No. 5,954,733 entitled "Suturing Instrument with Rotatably Mounted Needle Driver and Catcher"; U.S. Pat. No. 6,719,763 entitled "Endoscopic Suturing Device"; and U.S. Pat. No. 6,755,843 entitled "Endoscopic Suturing Device", all of which are incorporated by reference in their entireties for the teachings therein.

Assignees' U.S. Pat. Nos. 5,437,681, 5,540,705 and 6,923,819 disclose a suturing device with thread management comprising a protective cartridge, suturing needle and needle rotation drive, the disclosures of which are hereby incorporated by reference. The devices described in the above-mentioned patents and patent application comprise a mechanism for driving a protected needle however, the needle is rotated about an axis that is parallel to the axis of the device. In addition, the orientation and size of the suturing device makes it difficult to visualize and cumbersome to use for MIS.

Therefore, there remains a need in the art for a minimally invasive suturing device that is easily manipulated within the small diameter of the cannula; functions in an environment characterized by limited space, limited visualization, and limited mobility; mimics the preferred method of suturing used by surgeons; permits the surgeon to secure and tie knots quickly and with controlled tension; places continuous stitches; and protects user's from accidental needle sticks during needle handling, as well as internal organs and vessels, from inadvertent needle-pricks.

SUMMARY

Advantages of the present invention will be set forth in and become apparent from the description that follows. Additional advantages of the invention will be realized and attained by the methods and systems particularly pointed out in the written description and claims hereof, as well as from the appended drawings.

To achieve these and other advantages and in accordance with the purpose of the invention, as embodied herein, the invention includes a needle loader. The needle loader includes a generally planar needle supporting surface, a hub configured and adapted for receiving a generally toroidally shaped suturing needle around the hub, and means for retaining a suturing needle in a fixed toroidal rotational position with respect to the hub about a center axis of needle rotation. Generally, a needle mounted around the hub is selectively disposable on and removable from the hub.

In accordance with a further aspect, the loader may further include an opening for retaining suture material attached to a suturing needle. The opening may include a groove defined through the needle supporting surface. The needle loader may further include a guard for preventing access to the point of a suturing needle to protect the needle and/or to prevent accidental needle sticks. The needle loader may further include a generally toroid-shaped needle disposed on the needle loader. The needle may include suture material attached thereto. In accordance with one embodiment, the loader, needle and suture may be disposed in sterilizable packaging. In accordance with a preferred embodiment, the hub may be adapted and configured to be received by a portion of a suturing device. The needle loader preferably includes medical grade sterilizable polymeric material.

The invention also provides a system. The system includes a suturing device. The suturing device includes an elongate body having a suturing head at a distal end thereof, the suturing head defining a tissue receiving gap, wherein the suturing device is adapted and configured to direct a generally toroid-shaped needle in a circular track around the tissue receiving gap. The system also includes a needle loader. The needle loader includes a generally planar needle supporting surface, a hub configured and adapted for receiving a generally toroidally shaped suturing needle around the hub, means for retaining a suturing needle in a fixed toroidal rotational position with respect to the hub, wherein a needle mounted around the hub is selectively disposable on and removable from the hub, and a generally toroid-shaped needle disposed on the needle loader.

In accordance with one embodiment of the system, the hub is preferably adapted and configured to be received by the tissue receiving gap of the suturing device to facilitate transfer of the needle from the needle loader to the suturing device. The loader and needle may be disposed in sterilizable packaging. Furthermore, a portion of the suturing device may be adapted to be received by a gap defined between the needle and the loader.

The invention also provides a method. In accordance with one embodiment, the method includes the step of providing a suturing device as described above. The method further includes providing a needle loader having a needle mounted thereon, as described herein. The method also includes the step of transferring the needle from the needle holder to the suturing device. If desired, the hub of the needle loader may be inserted into the tissue receiving gap of the suturing device, and a portion of the suturing device may be displaced to retain the needle to facilitate transfer of the needle to the suturing device.

It is to be understood that the foregoing general description and the following detailed description are exemplary and are intended to provide further explanation of the invention claimed. The accompanying drawings, which are incorporated in and constitute part of this specification, are included to illustrate and provide a further understanding of the method and system of the invention. Together with the description, the drawings serve to explain principles of the invention.

DETAILED DESCRIPTION OF THE PREFERRED EMBODIMENT

Reference will now be made in detail to the present preferred embodiments of the invention, examples of which are illustrated in the accompanying drawings. The method and corresponding steps of the invention will be described in conjunction with the detailed description of the system.

Devices made in accordance with the related patent applications as incorporated by reference herein require the use of suturing needles that are advanced about a circular track. While these needles (having sutures attached) can be installed manually either before or during a surgical procedure, it is advantageous to provide devices and methods to make installation of these needles into the suturing devices both easier and safer. Accordingly, the instant disclosure provides exemplary devices and techniques for loading needles into such suturing devices.

Figure 1:
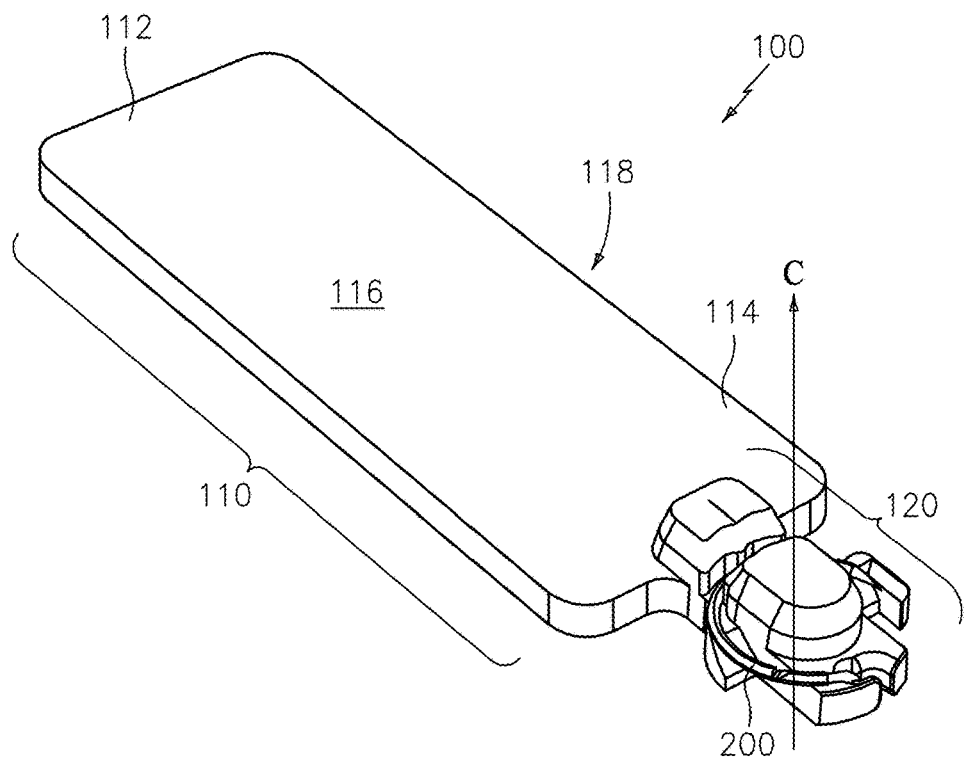
FIG. 1 is an isometric view of a suturing needle loader made in accordance with a first aspect of the present invention.
Figure 2:
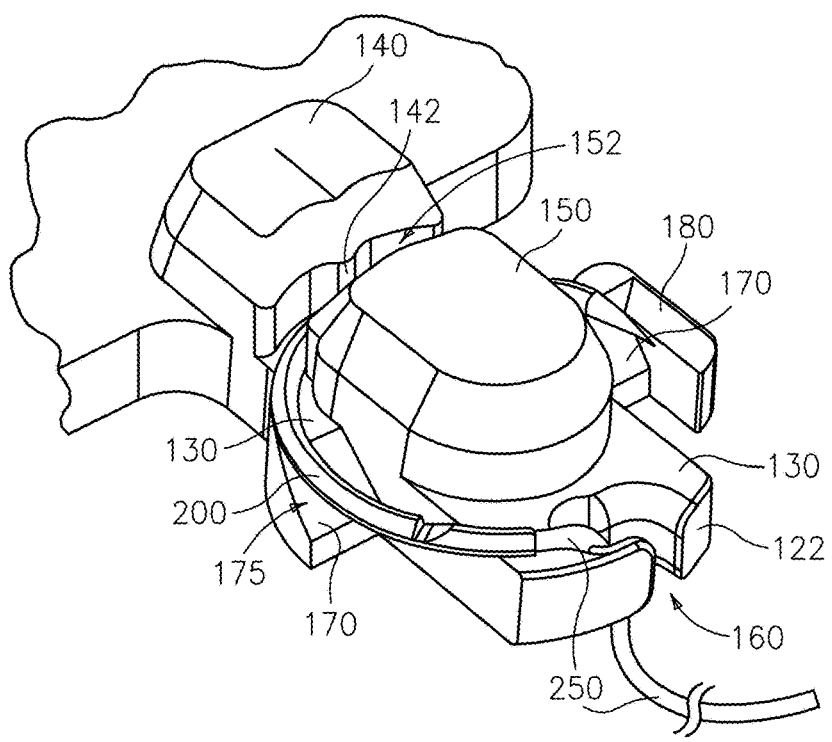
FIG. 2 is an enlarged isometric view of a portion of the needle loader of FIG. 1.

For purposes of illustration and not limitation, as illustrated in FIGS. 1-2, in accordance with one embodiment, a needle loader 100 is provided that is adapted and configured to load a suturing needle into a suturing device such as that described in U.S. patent application Ser. No. 11/231,135.

As depicted, needle loader 100 includes a generally planar proximal region 110 and a distal region 120. Proximal region includes a proximal end 112, a distal end 114 and generally planar opposed faces 116, 118. An operating room technician or nurse can grip loader 100 by the opposing faces 116, 118 to facilitate loading a needle 200 into a suturing device. If desired, faces 116, 118 may be textured to enhance gripping. As will be appreciated by those of skill in the art, proximal region 110 can be any suitable shape (e.g., having a round, elliptical, rectangular or other cross-section) and need not be generally planar. However, use of a generally planar proximal region is preferred for ease of manufacturing and use.

As depicted, distal region 120 of needle loader includes a needle supporting surface 130 a retainer block 140 and hub 150 for holding a needle 200 in position. The needle defines a center axis of rotation of needle C that passes through hub 150. As depicted, block 140 and hub 150 cooperate to define a needle retention channel 152 for receiving needle 200. If desired, a further extended bearing surface 142 may be included. In accordance with a preferred embodiment, needle 200 is installed into loader 100 by an interference fit between hub 150 and bearing surface 142. The interference fit retains suturing needle 200 in a fixed toroidal rotational position with respect to hub 150. The tolerance between needle 200 and loader 100 is preferably sufficient to prevent needle 200 from falling out if the loader is inverted, but still sufficient to permit needle 200 to be removed with relative ease during installation. As further depicted in FIG. 2, a suture retention groove 160 is defined in the distal end 122 of the distal region 120 of the loader 100. groove 160 is adapted and configured to receive a suture 250 therein to maintain the orientation of suture 250 (and of needle 200) when installing needle in a suturing device using loader 100.

Figure 3:
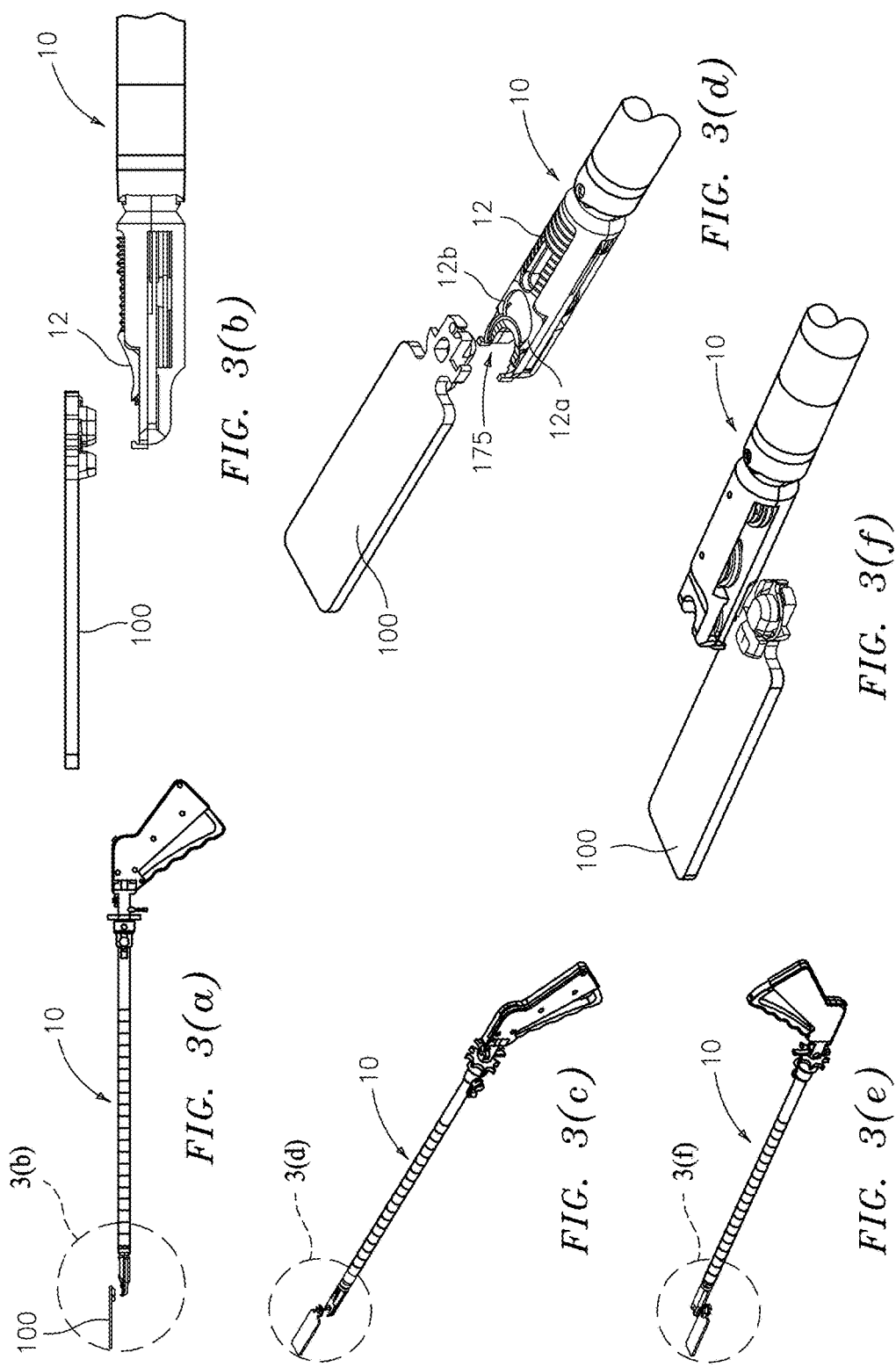
FIGS. 3(a)-3(f) are exploded isometric views depicting using the needle loader of FIG. 1 to load a needle into an exemplary suturing device.
Figure 4:
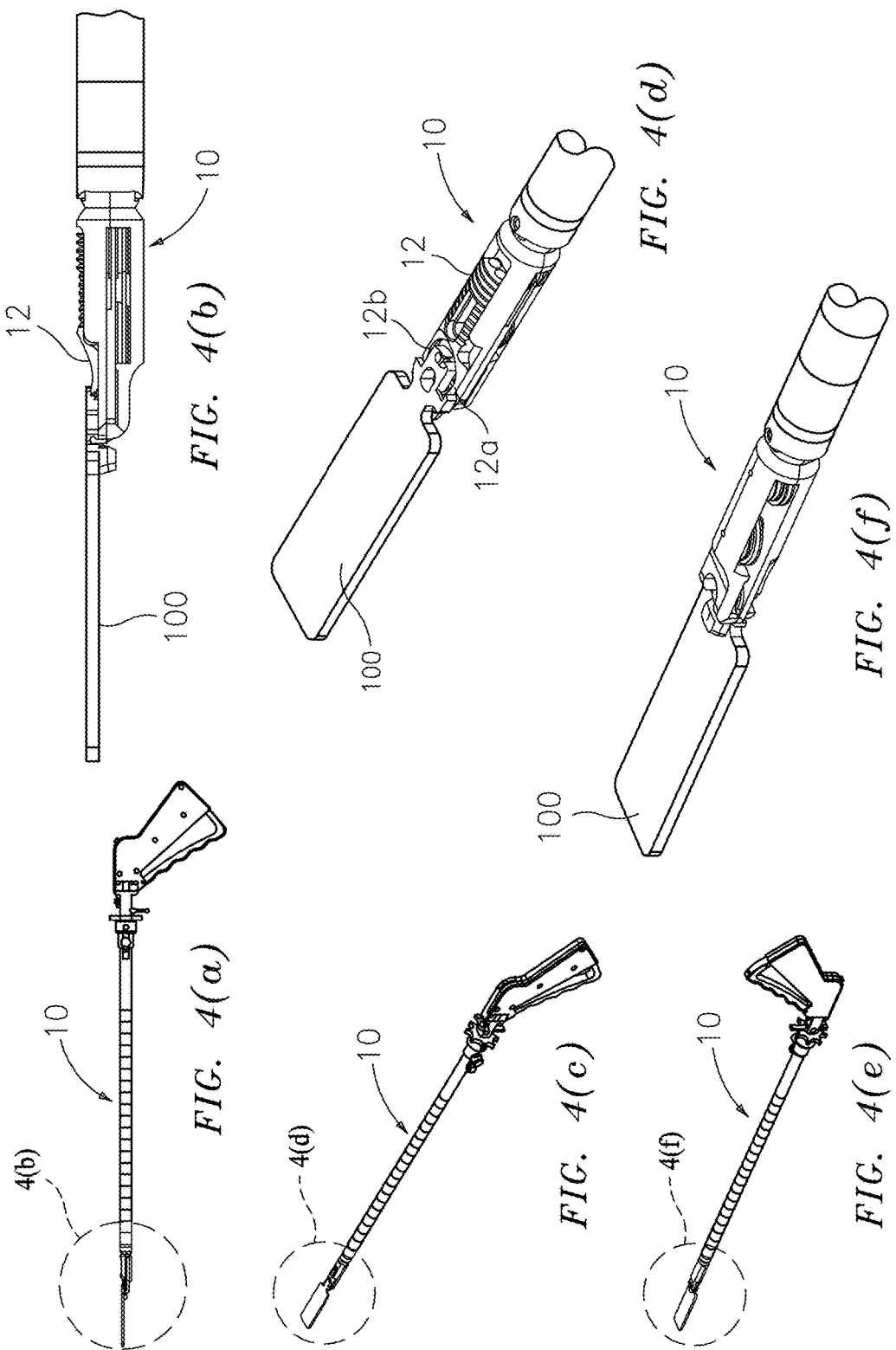
FIGS. 4(a)-4(f) are isometric views depicting using the needle loader of FIG. 1 to load a needle into an exemplary suturing device wherein the needle loader and suturing device are engaged.

With further reference to FIG. 2, if desired, inclined surfaces 170 may be provided to facilitate mating of the loader with a suturing device 10 (as depicted in FIGS. 3 and 4). As further depicted in FIG. 2, a guard may be provided to protect the point of needle 200 from damage, and to prevent accidental needle sticks while handling loader 100. Needle 200 is thus preferably placed in a rotational orientation with respect to loader 100 that places the point of the needle 200 behind the guard.

FIGS. 3(a)-3(f) and 4(a)-4(f) depict exemplary use of loader 100 with respect to a suturing device 10. FIGS. 3(a)-3(f) depict exploded views of loader 100 with respect separated from suturing device 10. By way of contrast, FIGS. 4(a)-4(f) depict views of loader 100 inserted into suturing device 10. In order to install a needle, retractable cover portion 12 of suturing device 10 is retracted proximally in order to expose a circular track into which needle 200 is to be installed. Next, loader 100 is inverted and aligned with a tissue receiving gap 150 defined in the distal end of the suturing device. Specifically, block 140 and hub 150 are received by the tissue receiving gap 150, such that the needle 200 is aligned with and received by the semicircular needle track of the suturing device 10. Next, the cover 12 is advanced distally to cover at least a portion of the needle 200, preventing the needle from being withdrawn with the loader 100. If desired, distal portions 12a, 12b of cover 12 can engage surfaces 170 of loader to help drive needle off of loader 100. Stated another way, distal portions 12a, 12b can be received by the gap 175 defined between needle 200 and surfaces 170. The loader 100 is then withdrawn, leaving the generally toroidal suturing needle 200 installed in the suturing device 10. Suture 250 is removed from groove 160, cover 12 is advanced into its distal position, and suturing device 10 is ready for use.

It will be appreciated that loader 100 can operate in a variety of manners. For example, it will be appreciated by those of skill in the art that loader 100 can be configured to selectively release needle 200 into a needle track, such as by configuring loader 100 to be flexed by an operator to cause channel 152 to widen, thereby releasing needle. Similarly, a pusher can be provided (such as in the form of a pin terminating in a button) disposed in an opening defined through loader 100 into track 152 (not depicted).

It will be further appreciated by those of skill in the art that loader can take on a variety of other configurations to accomplish a similar result. For example, instead of a groove 160, a hole (not depicted) can be provided to guide suture 250. However, it will be recognized that a groove 160 is preferred for ease of use, since the entire length of suture 250 need not pass through groove 160 after installing needle 200 in a suturing device 10. However, use of a hole instead of a groove would require that the entire length of suture 250 be pulled through the hole. By way of further example, if desired, planar portion 110 of loader can be provided with a layer of resilient material (e.g., foam or elastomeric material) to receive a used suturing needle to facilitate disposal and to reduce risk of needle sticks from used needles.

Loader 100 is preferably made from a resilient material (e.g., a polymeric material) that permits a suitable interference fit for needle 200. In accordance with one embodiment, loader is made from medical grade sterilizable polymeric material. However, it will be appreciated that any suitable material may be used to make loader 100. Loader 100 may be made with any known manufacturing techniques known by those of skill in the art, such as injection molding, stamping and the like. Needle 200 may be installed in loader 100 in a variety of ways. For example, needle 200 may be installed manually. In accordance with another embodiment, needle 200 may be installed automatically by a suitably machine adapted and configured for such a particular purpose.

Figure 5:
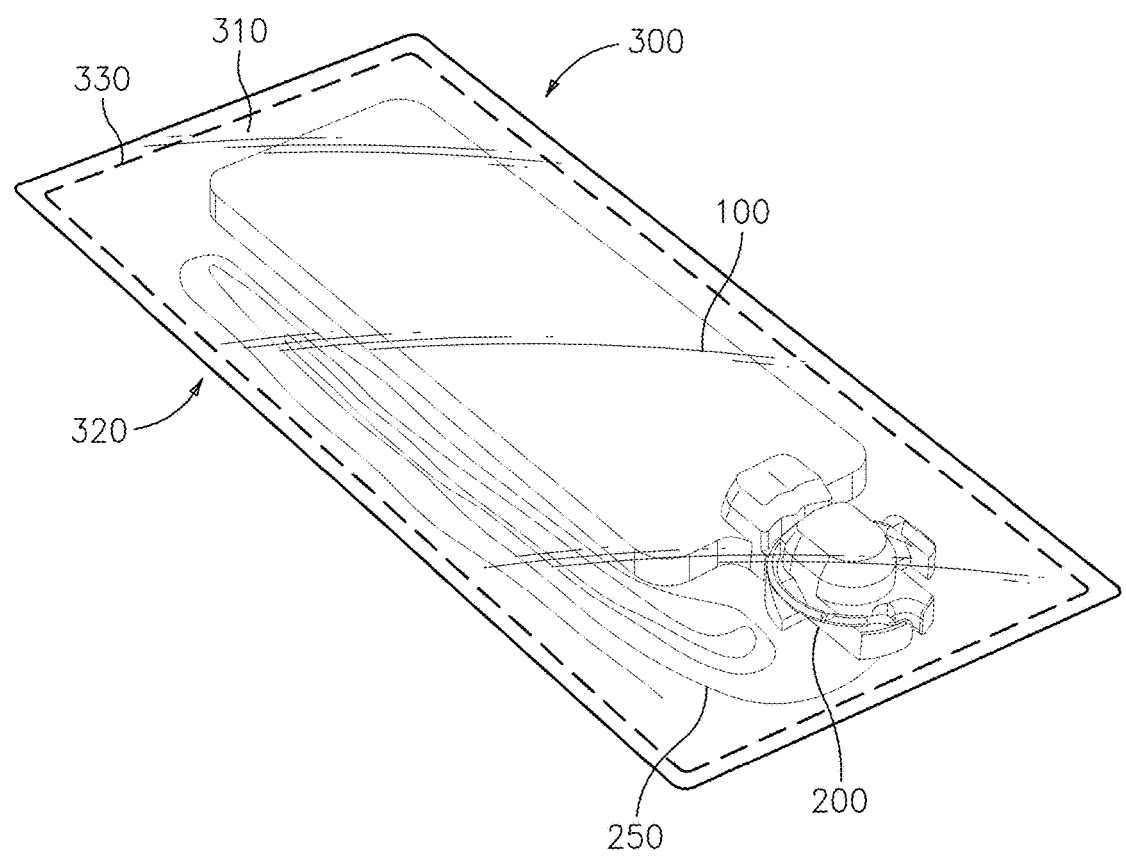
FIG. 5 is an isometric view of a sterilizable packaging kit provided in accordance with the present invention.

For purposes of further illustration and not limitation, as embodied herein, in accordance with a further embodiment, a packaged medical device is provided including a loader, a needle, and suture material. As depicted in FIG. 5, the loader 100, needle 200 and suture material 250 can form the components of a sterile kit 300, packaged in appropriate plastic/reinforced paper material 310, 320, which preferably can be peeled open to lay out the components onto a sterile field. The top web 310 of the package can be thermoformable transparent plastic film, such as polyamide/polyethylene or polypropylene/polyethylene. This allows the contents of the sealed package to be visible. The bottom web 320 can be sterilizable paper or similar material, such as Tyvek® material, with a basic weight of about 60 gm/m$^2$ or more, allowing it to be permeable to sterilizing gas, so that the loader 100, needle 200 and suture material 250 can be sterilized from within the package. The top and bottom webs 310, 320 are sealed along the periphery of the package using a suitable adhesive or other means. The package 300 preferably can be opened by hand, using peel-open corners and peelable seams 330. It will be recognized by those of skill in the art that proximal portion 110 of loader 100 may be shortened to facilitate packaging loader as described herein.

The methods and systems of the present invention, as described above and shown in the drawings, provide for improved techniques for loading suturing needles into suturing devices. It will be apparent to those skilled in the art that various modifications and variations can be made in the device and method of the present invention without departing from the spirit or scope of the invention. Thus, it is intended that the present invention include modifications and variations that are within the scope of the subject disclosure and equivalents.

What is claimed is:
1. A method of loading an arcuate needle into a suturing device, comprising:
 a) providing a needle loader having an arcuate needle disposed around a hub;
 b) providing a suturing device having a circular needle track for accommodating said needle, said circular needle track having a first end and a second end separated by a tissue accommodation gap configured to receive tissue to be sutured;
c) introducing said hub of said needle loader into said tissue accommodation gap of said suturing device;
d) transferring said needle from said hub to said needle track by pushing said arcuate needle into said needle track along a direction that is perpendicular to a plane defined by said needle track;
e) removing said hub from said needle track; and
f) operating said suturing device to perform a suturing operation using said arcuate needle.

2. The method of claim 1, further comprising guiding movement of a suture attached to said arcuate needle by providing an opening on said needle loader that receives said suture therethrough.

3. The method of claim 2, wherein said opening includes a groove.

4. The method of claim 2, wherein said opening includes a hole.

5. The method of claim 1, wherein said needle loader, arcuate needle, and a length of suturing material attached to the arcuate needle is provided in the form of a sterile kit.

6. The method of claim 5, wherein said sterile kit is packaged in a sterile package.

7. The method of claim 6, wherein said sterile package is configured to be peeled open to lay out the needle loader, needle and suture onto a sterile field.

8. A method of loading an arcuate needle into a suturing device, comprising:
a) providing a needle loader having an arcuate needle disposed on a hub;
b) providing a suturing device having a circular needle track for accommodating said needle, said circular needle track having a first end and a second end separated by a tissue accommodation gap configured to receive tissue to be sutured;
c) introducing said hub of said needle loader into said tissue accommodation gap of said suturing device;
d) transferring said needle from said hub to said needle track wherein a cover covering said needle track is removed prior to transferring said arcuate needle into said needle track;
e) removing said hub from said needle track; and
f) operating said suturing device to perform a suturing operation using said arcuate needle.

9. The method of claim 8, further comprising partially covering said needle with said cover when said needle is disposed in said needle track to facilitate removal of said needle from said hub.

10. The method of claim 8, wherein said arcuate needle is disposed around said hub.

11. The method of claim 10, wherein said transferring step is effectuated by pushing said arcuate needle into said needle track along a direction that is perpendicular to a plane defined by said needle track.

12. A method of loading an arcuate needle into a suturing device, comprising:
a) providing a needle loader having an arcuate needle disposed on a hub;
b) providing a suturing device having a circular needle track for accommodating said needle, said circular needle track having a first end and a second end separated by a tissue accommodation gap configured to receive tissue to be sutured;
c) introducing said hub of said needle loader into said tissue accommodation gap of said suturing device; and
d) transferring said needle from said hub to said needle track by selectively releasing said arcuate needle into said needle track by manipulating said needle loader;
e) removing said hub from said needle track; and
f) operating said suturing device to perform a suturing operation using said arcuate needle.

13. The method of claim 12 wherein said arcuate needle is disposed around said hub.

14. The method of claim 13, wherein said transferring step is effectuated by pushing said arcuate needle into said needle track along a direction that is perpendicular to a plane defined by said needle track.

15. A method of loading an arcuate needle into a suturing device, comprising:
a) providing a needle loader having an arcuate needle disposed on a hub;
b) providing a suturing device having a circular needle track for accommodating said needle, said circular needle track having a first end and a second end separated by a tissue accommodation gap configured to receive tissue to be sutured;
c) introducing said hub of said needle loader into said tissue accommodation gap of said suturing device; and
d) transferring said needle from said hub to said needle track by pushing a button to transfer said arcuate needle into said needle track;
e) removing said hub from said needle track; and
f) operating said suturing device to perform a suturing operation using said arcuate needle.

16. The method of claim 15, wherein said arcuate needle is disposed around said hub.

17. The method of claim 16, wherein said transferring step is effectuated by pushing said arcuate needle into said needle track along a direction that is perpendicular to a plane defined by said needle track.

18. A method of loading an arcuate needle into a suturing device, comprising:
a) providing a needle loader having an arcuate needle disposed on a hub, wherein the arcuate needle is installed on said hub automatically using a needle loader machine;
b) providing a suturing device having a circular needle track for accommodating said needle, said circular needle track having a first end and a second end separated by a tissue accommodation gap configured to receive tissue to be sutured;
c) introducing said hub of said needle loader into said tissue accommodation gap of said suturing device;
d) transferring said needle from said hub to said needle track;
e) removing said hub from said needle track; and
f) operating said suturing device to perform a suturing operation using said arcuate needle.

19. The method of claim 18, wherein said arcuate needle is disposed around said hub.

20. The method of claim 19, wherein said transferring step is effectuated by pushing said arcuate needle into said needle track along a direction that is perpendicular to a plane defined by said needle track.

* * * * *